United States Patent [19]

Nomura et al.

[11] Patent Number: 5,154,714
[45] Date of Patent: Oct. 13, 1992

[54] ABSORBENT PANEL FOR BODY FLUID ABSORPTIVE GARMENTS

[75] Inventors: Hironori Nomura, Iyomishima; Takamitsu Igaue, Kawanoe; Junji Shinohara, Iyomishima; Tsutomu Shiroto; Hiroyuki Tanji, both of Kawanoe, all of Japan

[73] Assignee: Uni-Charm Corporation, Ehime, Japan

[21] Appl. No.: 647,257

[22] Filed: Jan. 29, 1991

[30] Foreign Application Priority Data

Jan. 29, 1990 [JP] Japan .................................. 2-20111

[51] Int. Cl.$^5$ .......................................... A61F 13/15
[52] U.S. Cl. .................... 604/366; 604/368; 604/370; 604/379; 604/385.1
[58] Field of Search .............. 604/358, 365-384, 604/385.1; 424/103, 195, 198, 218, 220, 296, 908.8; 156/308.2, 308.4, DIG. 21, 167

[56] References Cited

U.S. PATENT DOCUMENTS

| | | | |
|---|---|---|---|
| 3,420,235 | 1/1969 | Harmon | 604/366 |
| 3,886,942 | 6/1975 | Bernardin | 604/366 |
| 4,100,324 | 7/1978 | Anderson et al. | 604/370 |
| 4,217,901 | 8/1990 | Bradstreet et al. | 604/371 |
| 4,219,024 | 8/1980 | Patience et al. | 604/366 |
| 4,304,234 | 12/1981 | Hartmann | 604/372 |
| 4,333,463 | 6/1982 | Holtman | 604/378 |
| 4,568,344 | 2/1986 | Suzuki et al. | 604/396 |
| 4,590,114 | 5/1986 | Holtman | 604/370 |
| 4,828,888 | 5/1989 | Hermansson | 604/379 |
| 4,931,352 | 6/1990 | Marshall et al. | 604/378 |
| 5,052,357 | 10/1991 | Winebarger | 604/366 |

FOREIGN PATENT DOCUMENTS

| | | | |
|---|---|---|---|
| 1186499 | 5/1985 | Canada | 604/370 |
| 0391727 | 3/1990 | European Pat. Off. | 601/378 |
| 2525210 | 12/1976 | Fed. Rep. of Germany | 604/366 |
| 1179181 | 8/1986 | Japan | 604/378 |
| 2061339 | 5/1981 | United Kingdom | 664/370 |

Primary Examiner—David Isabella
Assistant Examiner—K. Reichle
Attorney, Agent, or Firm—Fred Philpitt

[57] ABSTRACT

Here is an absorbent panel for body fluid absorptive garments such as a disposable diaper formed from a mixture of at least fibrous or granular liquid-absorptive material and thermoplastic fibers being compressed to a uniform thickness wherein said thermoplastic fibers are welded to each other with a welding density of their cross points to be higher in a crotch zone than in the remaining zone and to provide a tensile strength correspondingly higher in said crotch zone than in said remaining zone.

3 Claims, 2 Drawing Sheets

ABSORBENT PANEL FOR BODY FLUID ABSORPTIVE GARMENTS

BACKGROUND OF THE INVENTION

The present invention relates to an absorbent panel for body fluid absorptive garments and, more particularly, to such absorbent panel used in disposable diapers, disposable training pants and the like.

A mixture of fluffy pulp, water-insoluble polymer granules of high water absorptivity and hydrophilic or hydrophobic fibers has been conventionally used to form the absorbent panel of the above-mentioned type, wherein said mixture as a whole has been compressed or embossed to improve its absorptivity/diffusibility and shape holding ability.

However, the absorbent panel of the prior art still has a problem, concerning the shape holding ability and there has often occurred so-called shape loss during use of the associated garments particularly in the proximity of the user's crotch in which the panel is affected by a deforming force due to movement of the user.

Accordingly, it is an object of the invention to provide an absorbent panel positioned in the proximity of the user's crotch but so constructed that the portion being inevitably prone to said deforming force due to the user's movement is more resistive to the shape loss than the remaining portion of the absorbent panel.

SUMMARY OF THE INVENTION

The object set forth above is achieved, in accordance with the present invention, by an absorbent panel for body fluid absorptive garments formed from a mixture of at least fibrous or granular liquid-absorbent material and thermoplastic fibers by compressing this mixture substantially to a uniform thickness, said absorbent panel being characterized by that said thermoplastic fibers are welded to each other with a welding density of their cross points (i.e. the number of welded cross points) adjusted to be higher in the crotch zone than in the remaining zone and to provide a tensile strength correspondingly higher in said crotch than in said remaining zone.

Preferably the welding density of said thermoplastic fibers in zones extending from the both sides of the crotch zone therealong to longitudinally opposite ends also is adjusted to be higher than in the remaining zone so that said zones also have a tensile strength correspondingly higher than that in said remaining zone.

The absorbent panel constructed according to the invention as has been mentioned above is well resistant to a significant shape loss particularly in the crotch zone even under a deforming force due to the user's movement and eliminates discomfort to wear as well as a decrease in absorptivity due to the shape loss, since said crotch zone has a higher tensile strength. The particular zones of the absorbent panel inclusive of said crotch zone have a relatively high rigidity because these particular zones have a higher tensile strength, but the remaining zone has a relatively low tensile strength and, on average, comfortable wear can be assured.

BRIEF DESCRIPTION OF THE DRAWINGS

The invention will become more readily apparent from the following description of a preferred embodiment thereof shown by way of example only, in the accompanying drawings, in which.

PREFERRED EMBODIMENT OF THE INVENTION

Figure 1:
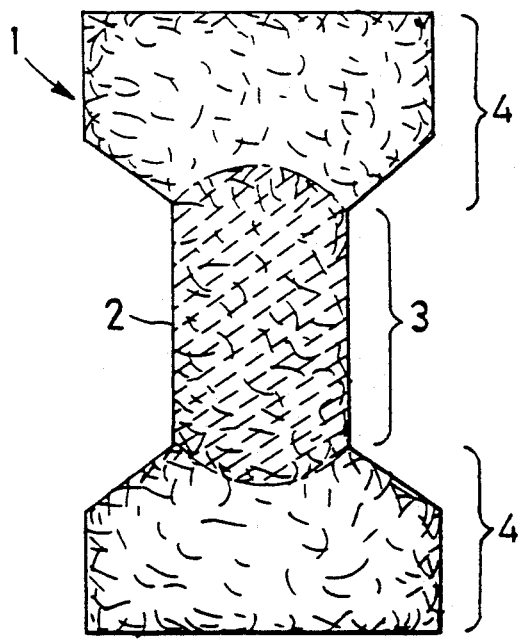
FIG. 1 is a plan view of an absorbent panel for disposable diaper constructed as an embodiment of the invention.

Referring to FIG. 1, one embodiment of the absorbent panel constructed in accordance with the invention is shown in a plan view. The absorbent panel 1 is composed of fluffy pulp, water absorptive polymer granules and thermoplastic crimped fibers mixed together, and presents a so-called hourglass-shape formed along both sides of a crotch zone with notches 2.

The absorbent panel 1 is formed by compressing the above-mentioned mixed material substantially to a uniform thickness wherein said thermoplastic crimped fibers are welded together at their cross points so that the absorbent panel 1 has a thickness restoring ability of 30% or higher with respect to its compressed state when its water absorption reaches a saturation point. Furthermore, in the absorbent panel 1, a welding density of cross points of said thermoplastic crimped fibers is adjusted to be higher in the crotch zone 3 adapted to be positioned in the proximity of the corresponding crotch zone of the associated garments such as disposable diaper or disposable training pants when it is put on a user's body than the other zone 4 so that the absorbent panel 1 presents a tensile strength higher in said crotch zone 3 than in the remaining zones 4.

Said thermoplastic crimped fibers may be a composite of two components having different melting points, such as polyethylene-polypropylene or polyethylene-polypropylene-polyethylene composite film which was treated by a scratching roller provided therearound with a plurality of scratching needles to produce short fibers which are then crimped by heat treatment, or may be polyethylene-polypropylene composite fibers of the side-by-side type or the sheath-core type which are crimped by heat treatment. Such fibers extend in three directions and entangle together, forming a three dimensional network structure among said fluffy pulp and polymer granules, wherein said fibers are welded to each other with the density of their cross points through the low m.p. component such as the polyethylene component and supported by the high m.p. component such as polypropylene serving as the framework. This network structure has a high compression elasticity and significantly contributes to the thickness restoring ability by water absorption of the absorbent panel 1. For such a contribution, it is essential not only that the fibers are crimped and partially welded together to form the three dimensional network structure, but also that the amount and fincress of these fibers are appropriate. The appropriate amount of the fibers is 10 to 70% by weight and preferably 30 to 40% by weight. So far as the ability of thickness restoration from the compressed state is concerned, the amount of the fibers should be increased. However, it is critical to assure a desired amount of said fluffy pulp and polymer granules providing a water holding function within the absorbent panel 1 and therefore the maximum amount of the fibers should be limited to 70% by weight. The appropriate finecress is $3d$ or higher and preferably 10 to 50d. Crimping may be effected by said heat treatment or by a mechanical treatment, for example, by guiding the fibers between heating rollers having therearound wedges and grooves, respectively. The number of crimps is preferably 3 to 40/inch and the fiber length is preferably 30 to 60 mm.

Said fluffy pulp may be obtained by crushing or fibrillation of pulp sheet with the use of a garnet or the like so as to obtain fibers having a length less than 5 mm. The amount thereof to be mixed is 10 to 70% by weight and preferably 20 to 55% by weight.

Said polymer granules may be those commonly employed in a disposable diaper, menstrual napkin, etc. on account of their water-insolubility and significant water holding function. Useful polymer granules may be, for example, of those such as hydrolyte of bridged polyacrylate and acrylic acid-acrylic acid ester copolymer or of self-bridging polyacrylate-starch acrylonitrile graft copolymer. The amount thereof to be mixed is 5 to 50% by weight and preferably 10 to 40% by weight. These polymer granules may be bonded integrally with the fibers so that the crimped fibers forming the three dimensional network structure are intermittently covered with the polymer granules in spherical or elliptical shapes or the fibers extend through spherical or elliptical polymer granules which are intermittently distributed in the panel. Such bonding is effected, for example, by spraying the fibrous assembly with liquid monomers for polymerization.

The absorbent panel 1 composed of the mixed material as has been mentioned above will preferably have a density of 100 to 700 g/m$^2$ when it is associated with, for example, a disposable diaper or disposable training pants. In addition, the absorbent panel 1 assembled from said mixed material is preferably compressed in the direction of its thickness in the presence of a small amount of water or aqueous solution of binder so that the absorbent panel 1 has a density of 0.033 to 0.7 g/cm$^3$.

To assure that the welding density of said thermoplastic crimped fibers is higher in the crotch zone 3 than in the remaining zone of the absorbent panel and a correspondingly higher tensile strength than in the remaining zone 4, after said mixed material has been compressed, the crotch zone 3 of the absorbent panel 1 may be, for example, subjected to hot air blasting at a predetermined temperature while the remaining zone 4 may be substantially protected against the effect of such hot air blasting. It should be understood that this heat treatment may be utilized also to achieve the same effect as the previously mentioned crimping of the fibers by heat treatment.

Figure 2:
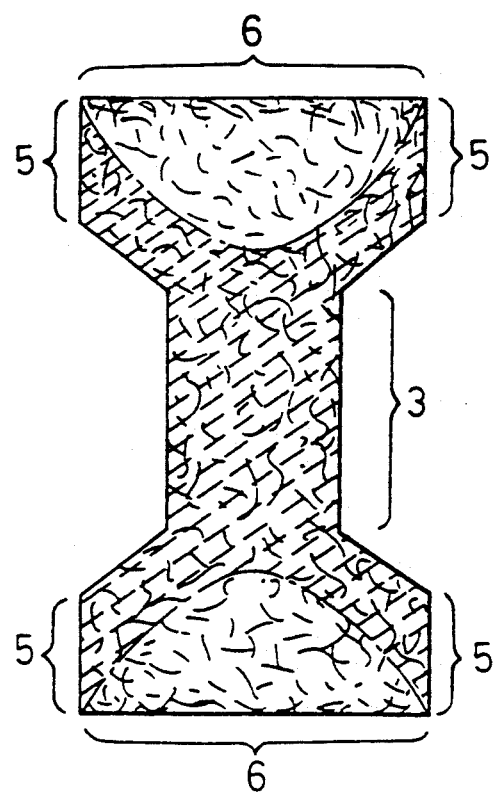
FIG. 2 is a plan view showing another embodiment of the absorbent panel.

In the embodiment shown by FIG. 2, the welding density of said thermoplastic crimped fibers not only in the crotch zone 3 but also zones 5 extending from the laterally both sides of the crotch zone 3 therealong to longitudinally opposite ends is adjusted to be higher than in the remaining zone 6 so that said zones 5 also have a tensile strength higher than in the remaining zone 6.

Figure 3:
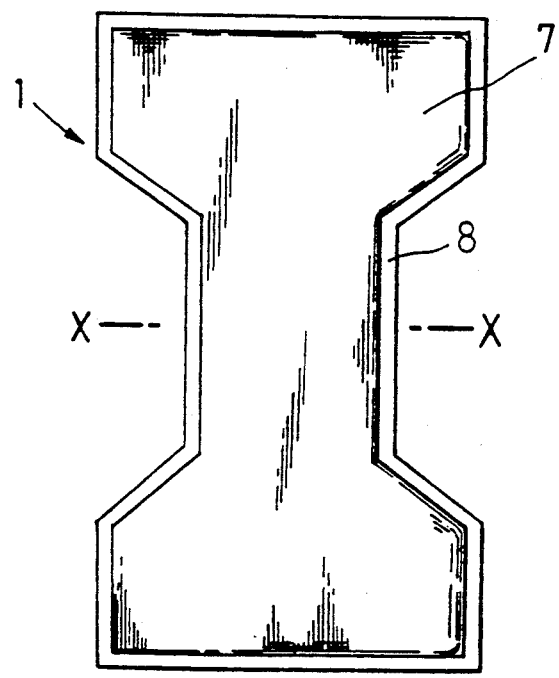
FIG. 3 is a plan view of the absorbent panel having top and bottom surfaces covered with tissue paper.
Figure 4:
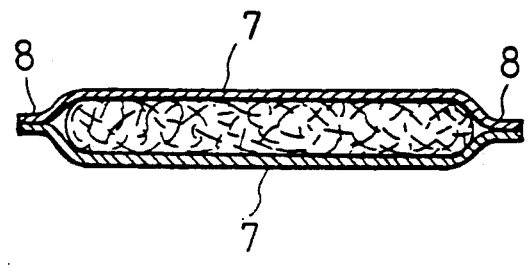
FIG. 4 is a sectional view taken along a line X—X in FIG. 3.

Referring to FIGS. 3 and 4, the top and bottom surfaces of the absorbent panel 1 as shown by FIG. 1 or 2 and having been subjected to said heat treatment are covered with sheets of tissue paper to for a cover 7 having water absorptivity and diffusibility, and these sheets of tissue paper are heat sealed along the peripheries thereof. This construction results in improving the shape hold of the absorbent panel 1 and, if desired, this assembly may be embossed from above downwardly on the sheets of tissue paper at desired locations of the absorbent panel 1 for further improvement of the shape hold as well as the tensile strength.

Though not shown, particularly in the crotch zone 3 required to have a high absorptivity, the content of said mixed material used in this zone 3 may be increased with respect to the remaining zone and then the absorbent panel 1 may be subjected to a substantially uniform compression in the direction of its thickness.

What is claimed is:

1. In a body fluid absorptive device said device including:
    (a) an absorbent panel or core (1) consisting of a central crotch zone (3) having two opposed sides and end zone (4, 6) extending outwardly from each side of said crotch zone (3), said crotch zone defining means for positioning adjacent the crotch of wearer to absorb body fluids, said absorbent panel or core (1) being composed of liquid-absorptive fibers or granules and thermoplastic fibers, and
    (b) a cover (7) surrounding said absorbent panel or core (1), the improvement in said device comprising that within said absorbent panel or core (1)
        (1) the liquid-absorptive fibers or granules and thermoplastic fibers are compressed to a substantially uniform thickness, and
        (2) the thermoplastic fibers in the crotch zone (3) of said absorbent panel or core (1) are welded to each other with the welding density of their cross points being higher than a welding density of the cross points in said end zones (4, 6) of said absorbent panel or core (1) so as to thereby provide a higher tensile strength in said crotch zone (3) than in the remainder of the absorbent panel or core (1).

2. A body fluid absorptive device according to claim 1 wherein said higher welding density is achieved by subjecting said crotch zone (3) to hot air blasting while protecting the remainder of the absorbent panel or core (1) against the effect of such hot air blasting.

3. A body fluid absorptive device according to claim 1 wherein the sides of said crotch zone are not parallel to each other but extend outwardly in a generally U-shaped configuration so that each side of said crotch zone includes two outwardly diverging leg sections (5) that partially surround said end zones (6).

* * * * *